(12) United States Patent
Demanze (10) Patent No.: US 9,588,074 B2
(45) Date of Patent: Mar. 7, 2017

(54) METHOD FOR MONITORING THE INTEGRITY OF A FLEXIBLE LINE EXTENDING THROUGH A FLUID EXPLOITATION FACILITY, AND ASSOCIATED FLEXIBLE LINE, KIT AND PRODUCTION PROCESS

(71) Applicant: Frédéric Demanze, Caudebec en Caux (FR)

(72) Inventor: Frédéric Demanze, Caudebec en Caux (FR)

(73) Assignee: TECHNIP FRANCE (FR)

( * ) Notice: Subject to any disclaimer, the term of this patent is extended or adjusted under 35 U.S.C. 154(b) by 340 days.

(21) Appl. No.: 14/366,558

(22) PCT Filed: Dec. 21, 2012

(86) PCT No.: PCT/EP2012/076784
§ 371 (c)(1),
(2) Date: Jun. 18, 2014

(87) PCT Pub. No.: WO2013/093068
PCT Pub. Date: Jun. 27, 2013

(65) Prior Publication Data
US 2014/0345740 A1    Nov. 27, 2014

(30) Foreign Application Priority Data
Dec. 21, 2011   (FR) .................................... 11 62146

(51) Int. Cl.
*F16L 55/00*   (2006.01)
*G01N 27/20*   (2006.01)
(Continued)

(52) U.S. Cl.
CPC .............. *G01N 27/20* (2013.01); *F16L 11/04* (2013.01); *F16L 11/127* (2013.01); *G01M 3/40* (2013.01);
(Continued)

(58) Field of Classification Search
CPC ......... G01M 3/18; G01M 3/243; F16L 57/06; B65G 53/66; B65G 53/523
(Continued)

(56) References Cited
U.S. PATENT DOCUMENTS 3,382,493 A * 5/1968 Loper, Jr. ................ G01M 3/18
138/104
4,312,383 A * 1/1982 Kleykamp ........... F16L 11/1185
138/103
(Continued)

FOREIGN PATENT DOCUMENTS

WO   WO 2009/070769 A1   6/2009
WO   WO 2011/027154 A1   3/2011

OTHER PUBLICATIONS

International Search Report dated Jan. 31, 2013 issued in corresponding International patent application No. PCT/EP2012/076784.

*Primary Examiner* — Patrick F Brinson
(74) *Attorney, Agent, or Firm* — Ostrolenk Faber LLP (57) ABSTRACT

A method including the provision of at least one wire sensor (54A) including a polymeric matrix and having greater electric conductivity than that of the tubular body (52). The method includes the measurement of an electric quantity representative of the integrity of the flexible line, in at least one measurement point (60A, 60B) located on the sensor (54A).

23 Claims, 5 Drawing Sheets

(51) Int. Cl.
    *G01M 3/40* (2006.01)
    *G01M 5/00* (2006.01)
    *F16L 11/127* (2006.01)
    *F16L 11/04* (2006.01)
(52) U.S. Cl.
    CPC ........ G01M 5/0025 (2013.01); G01M 5/0033 (2013.01); G01M 5/0083 (2013.01); *Y10T 29/49002* (2015.01)
(58) Field of Classification Search
    USPC ........................................ 138/104, 133, 152
    See application file for complete search history.

(56) References Cited

U.S. PATENT DOCUMENTS

| | | | | |
|---|---|---|---|---|
| 4,446,892 A * | 5/1984 | Maxwell | ................. | F16L 11/12 116/227 |
| 5,017,873 A * | 5/1991 | Rippingale | ............ | G02B 6/447 116/209 |
| 5,036,210 A * | 7/1991 | Goodman | ............ | B29C 47/0019 138/104 |
| 5,051,034 A * | 9/1991 | Goodman | ............ | B29C 47/0019 138/104 |
| 5,243,128 A | 9/1993 | Marcoz | | |
| 5,634,497 A * | 6/1997 | Neto | ...................... | F16L 11/088 138/104 |
| 6,092,558 A * | 7/2000 | Maccario | ................... | F16L 1/11 116/209 |
| 6,202,701 B1 * | 3/2001 | Gobl | ..................... | F16L 11/127 138/127 |
| 6,386,237 B1 * | 5/2002 | Chevalier | ............. | F16L 11/12 116/208 |
| 6,498,991 B1 * | 12/2002 | Phelan | .................... | G01M 3/18 138/104 |
| 6,933,438 B1 * | 8/2005 | Watts | .................. | B29C 47/0016 138/104 |
| 2008/0210329 A1 * | 9/2008 | Quigley | ................ | F16L 11/083 138/127 |

\* cited by examiner

METHOD FOR MONITORING THE INTEGRITY OF A FLEXIBLE LINE EXTENDING THROUGH A FLUID EXPLOITATION FACILITY, AND ASSOCIATED FLEXIBLE LINE, KIT AND PRODUCTION PROCESS

CROSS REFERENCE TO RELATED APPLICATIONS

The present application is a 35 U.S.C. §371 National Phase conversion of PCT/EP2012/076784, filed Dec. 21, 2012, which claims benefit of French Application No. 11 62146, filed Dec. 21, 2011, the disclosure of which is incorporated herein by reference. The PCT International Application was published in the French language.

TECHNICAL FIELD OF THE INVENTION

The present invention relates to a method for monitoring the integrity of a flexible line extending through a fluid exploiting facility, the flexible line including at least one tubular polymer body.

BACKGROUND OF THE INVENTION

The flexible line is advantageously a flexible pipe intended for conveying a fluid, in particular an underwater pipe capable of receiving a petroleum fluid in order to transfer this fluid from the bottom of a stretch of water to the surface. Such a flexible pipe is for example defined by the API 17J or API RP 17B standard of the American Petroleum Institute (API) and generally comprises from the inside to the outside, a carcass, a pressure sheath, at least one internal pressure-resistance armor for the transported fluid, at least one tensile-strength armor and one external protective sheath.

Alternatively, the flexible line is an umbilical intended for transporting a control fluid, electric power or an information signal. Such an umbilical is for example defined by the general standard API 17E and API RP 17I.

In facilities for exploiting a fluid, intended to collect hydrocarbons in the bottom of a stretch of water, it is known how to connect a bottom assembly to a surface facility by means of a flexible line as defined above.

In order to connect the line onto the surface structure, the line is immersed in the stretch of water, and an upstream end of the line is then moved up towards the surface structure with view to connecting it thereto.

In order to prevent the line from undergoing large torsions or flexures during this installation or during subsequent operation of the facility, the flexible line is engaged through a guide tube secured to the surface structure. This tube is designated by the term of <<I-Tube>> or <<J-Tube>> according to its shape.

During the ascent of the flexible line inside the tube, or during its operational use, outer abrasion of the sheath protecting the flexible line sometimes occurs. This abrasion is for example generated by the friction between the external face of the sheath and the internal face of the protective tube.

In certain critical cases, the abrasion at the surface may generate microcracks or a loss of integrity of the protective sheath, also called an external sheath. In this case, the metal elements located inside the sheath, and in particular the tensile armors, are capable of being corroded, which may have significant consequences on the mechanical strength of the flexible line over time.

It is therefore necessary to be able to easily check the mechanical integrity of such a pipe, in particular after introducing it in a protective tube, since any accessibility to the pipe then becomes impossible. Visual inspection is impossible for the portion of the pipe located in the protective tube.

WO2009/070769 describes a measurement method in which an optical sensor, formed by an optical fiber is integrated into the internal structure of a flexible pipe.

Optical measurements made on the optical fiber give the possibility of determining whether this fiber is mechanically degraded.

Such a method is however complicated and expensive to apply, since it requires an enhanced optical apparatus.

SUMMARY OF THE INVENTION

An object of the invention is to obtain a method for monitoring the integrity of a flexible line position through a fluid exploiting facility, which is simple to apply and inexpensive.

For this purpose, the subject-matter of the invention is a method of the aforementioned type, characterized in that the method comprises the following steps:

providing at least one wire sensor in contact with the tubular body, said or each sensor including a polymer matrix having an electric conductivity greater than that of the tubular body;

measuring an electric quantity representative of the integrity of the tubular body, in at least one measuring point located on the sensor.

The method according to the invention may comprise one or more of the following features, taken individually or according to a technically possible combination:

the flexible line is engaged through a protective tube present in the fluid exploiting facility, in particular a vertical tube secured to a surface structure of the facility, at least one portion of the sensor being positioned in the protective tube;

said or each sensor is embedded into the thickness of the tubular body or is attached on one face of the tubular body;

said or each sensor is made on the basis of an intrinsically conductive polymer matrix advantageously based on a polymer selected from polyacetylenes, polyanilines, polypyrrols, and polythiophenes;

said or each sensor is made on the basis of an insulating polymer matrix filled with conductive particles, the electrically conductive particles being in particular selected from carbon black particles, carbon nanotubes, graphene, metal particles or mixtures thereof;

it includes the putting of the first measuring point located on the sensor in contact with the first terminal of a device for measuring an electric quantity, and the putting of a second measuring point located on the sensor or on an additional sensor in contact with a second terminal of the measuring device, the measuring device being advantageously a multimeter, the electric quantity in particular being conductivity or resistivity;

it includes the injection of an electric signal into the sensor and the measurement of an electric signal having propagated through the sensor in at least one measuring point for determining the electric continuity of the sensor;

it includes the provision of at least one first wire sensor and of at least one second wire sensor in contact with the tubular body, each sensor including a polymer matrix having greater electric conductivity than that of the tubular body, the first sensor and the second sensor being at least spaced apart angularly relatively to each other, relatively to an axis of the tubular body;

at least one first downstream point of the first sensor, advantageously an end of the first sensor, is electrically connected with a second downstream point of the second sensor, advantageously one end of the second sensor, said or each measuring point being respectively located away from the first downstream point and away from the second downstream point;

it includes the putting of a first measuring point located on one of the first sensor and of the second sensor in contact with a first terminal of an apparatus for measuring an electric quantity, and the putting of a second measuring point located on one of the first sensor and of the second sensor in contact with a second terminal of the measuring apparatus, the measuring apparatus being advantageously a multimeter, the electric quantity in particular being conductivity or resistivity;

at least one portion of the first sensor and of the second sensor is located in the protective tube;

the polymer matrix of said or each sensor is solid over the whole length of the sensor.

The subject-matter of the invention is also a flexible line intended to be extended through a fluid exploiting facility, the flexible line comprising at least one sheath including a polymer tubular body, characterized in that the sheath includes at least one wire sensor in contact with the tubular body, each sensor including a polymer matrix and having greater electric conductivity than that of the tubular body.

A flexible line according to the invention may comprise one or more of the following features taken individually or according to any technically possible combination:

the tubular body contains or delimits a passage for circulation of fluid;

the sensor is made on the basis of an intrinsically conductive polymer, or of an insulating polymer filled with conductive particles;

it includes at least one first wire sensor and at least one second wire sensor in contact with the tubular body, said or each sensor including a polymer matrix and having greater electric conductivity than that of the tubular body, the first sensor and the second sensor being at least partly spaced apart angularly relatively to each other, relative to an axis of the tubular body, the first sensor and the second sensor advantageously extending facing each other, longitudinally relatively to the tubular body, in particular parallel with each other.

The subject-matter of the invention is also a measurement kit, characterized in that it includes a flexible line as described above, and an apparatus for measuring an electric quantity in at least one measuring point located on the sensor, the measuring apparatus being advantageously a measuring apparatus intended for measuring an electric quantity between two measuring points spaced apart from each other or an apparatus for measuring an electric signal propagating through the sensor.

The subject-matter of the invention is also a fluid exploiting facility through a stretch of water, of the type including:

a surface structure;

a protective tube, secured to the surface structure;

a flexible line as defined above, inserted through the tube;

an apparatus for measuring an electric quantity intended to be connected to at least one measuring point located on the wire sensor advantageously intended to be connected to a first measuring point on a first wire sensor and to a second measuring point on a second wire sensor.

The subject-matter of the invention is also a method for manufacturing a flexible line as described above, comprising the following steps:

extruding the polymer tubular body;

positioning at least one wire sensor in contact with the tubular body, said or each sensor including a polymer matrix and having greater electric conductivity than that of the tubular body.

The method according to the invention may comprise one or more of the following features, taken individually or according to any possible technical combination:

said or each sensor is co-extruded simultaneously with the tubular body so as to be positioned in the thickness or on one face of the tubular body;

said or each sensor is manufactured before extrusion of the tubular body, and it is then positioned in the thickness or on one face of the tubular body during extrusion of the tubular body.

BRIEF DESCRIPTION OF THE DRAWINGS

The invention will be better understood upon reading the description which follows, only given as example and made with reference to the appended drawings, wherein.

DESCRIPTION OF PREFERRED EMBODIMENTS

Figure 1:
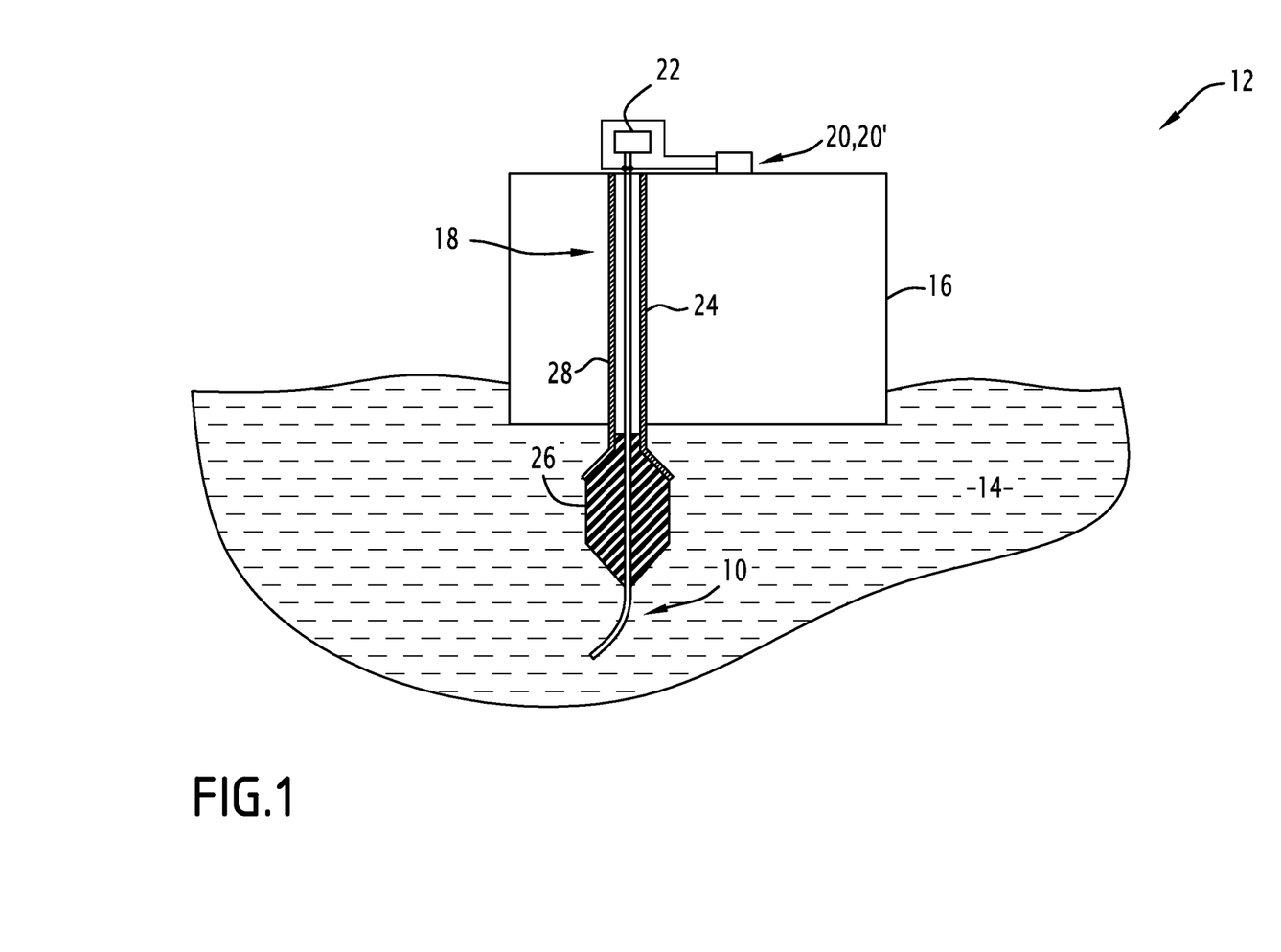
FIG. 1 is a schematic partial sectional view of a first fluid exploiting facility through a stretch of water, provided with a flexible line according to the invention.
Figure 2:
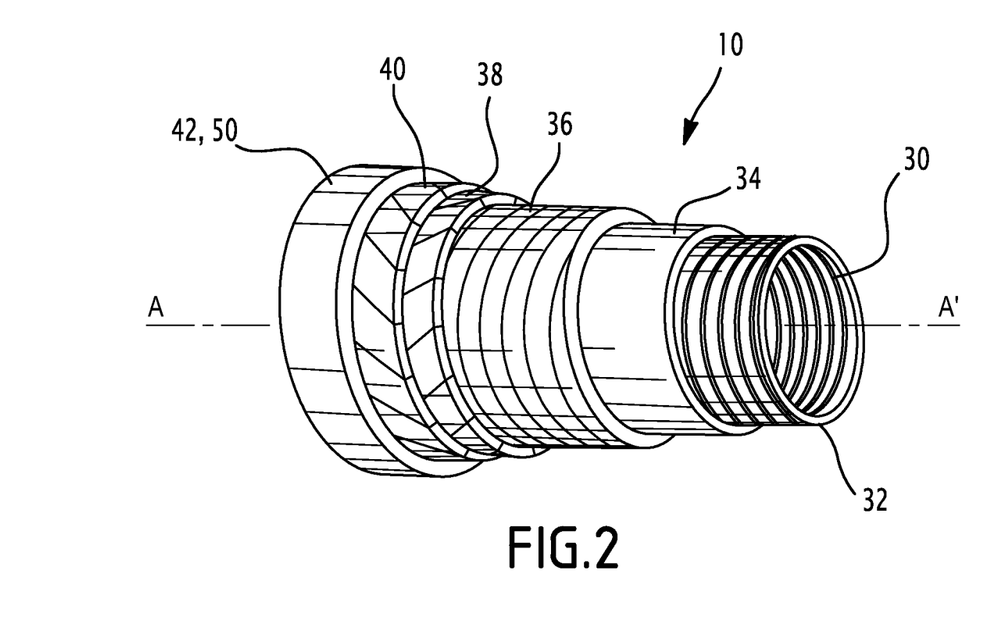
FIG. 2 is a schematic partial perspective of a flexible line example according to the invention.
Figures 3, 4:
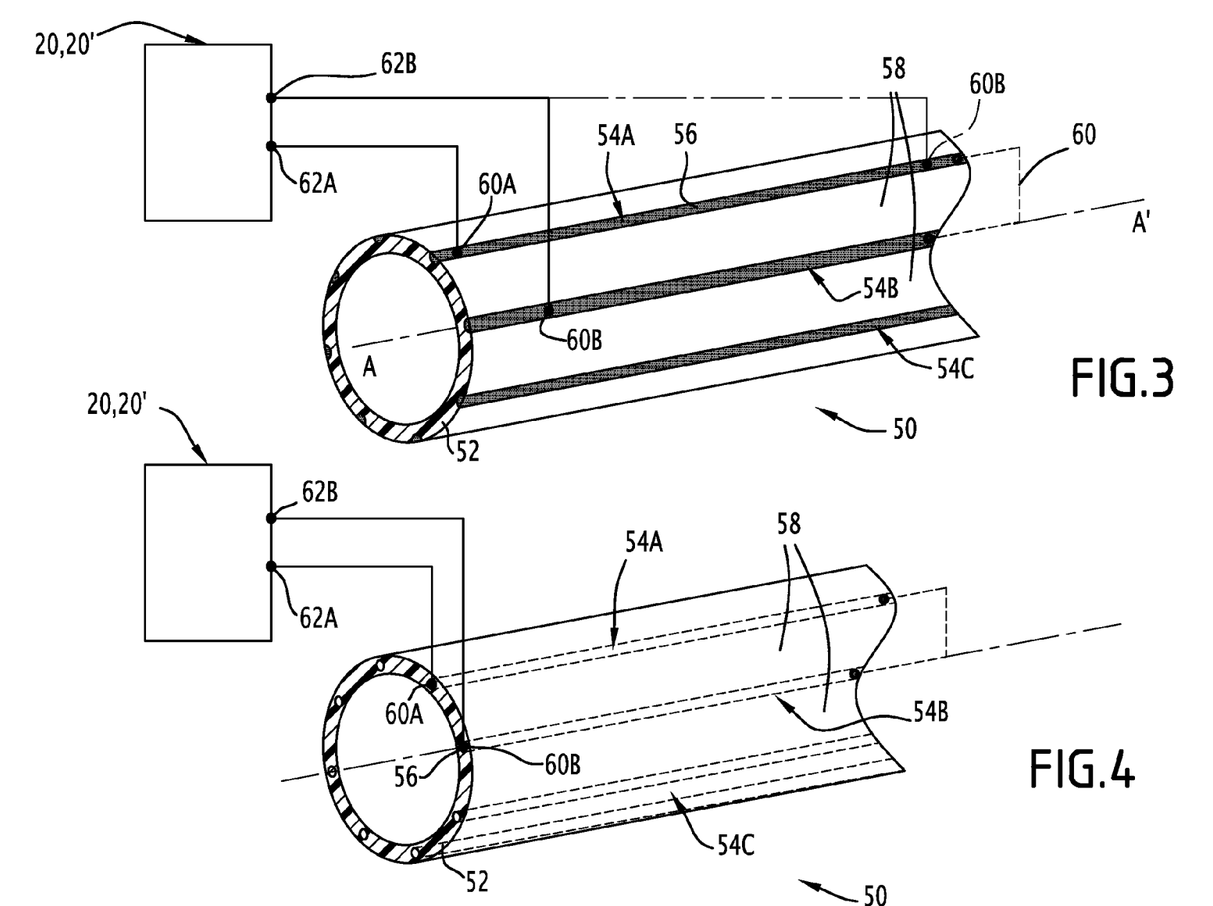
FIG. 3 is a partial perspective view of a first embodiment of an instrumented sheath for a flexible line according to invention.
FIG. 4 is a view similar to FIG. 3 of a second example of an instrumented sheath.

A first flexible line 10, provided with a partly conductive instrumented sheath according to the invention, is schematically illustrated by FIGS. 2 and 3. This flexible line 10 is intended to be used in a fluid exploiting facility 12 through a stretch of water 14 illustrated in FIG. 1.

The facility 12 is for example intended for collecting a fluid, in particular a hydrocarbon, taken from the bottom of the stretch of water 14 and/or for transferring this hydrocarbon to a transport ship.

The facility 12 includes a surface structure 16, a bottom assembly (not shown), located on the surface of stretch of water 14 and at least one flexible line 10 connecting the bottom assembly to the surface structure 16.

The facility 12 further includes a device 18 for guiding the flexible line 10 on the surface structure 16 and an apparatus 20; 20' for measuring information representative of the integrity of the flexible line 10.

The stretch of water 14 is for example a lake, a sea or an ocean. The depth of the stretch of water 14 at right angles to the floating structure 16 is for example comprised 15 meters and 4,000 meters.

The surface structure 16 is for example a floating structure. It is advantageously formed by a naval surface support, a semi-submersible rig, a vertical floating column (of the SPAR type), or ship for example of the FPSO (<<Floating Production, Storage and Offloading>>) type.

Alternatively, the surface structure 16 is a rigid structure of the fixed type of the <<jacket>> type or an oscillating structure secured to the sea bottom. It includes at least one connector 22 intended to be connected to a downstream end of the flexible line 10.

When the flexible line 10 is a pipe for transporting fluid, the connector 22 is advantageously a collector of the <<manifold>> type for collecting the fluid circulating through the flexible line 10.

The guiding device 18 includes a hollow rigid tube 24 secured to the structure 16 and a curvature limiter 26 mounted around the flexible line 10 for partly engaging into the hollow rigid tube 24.

In the example illustrated in FIG. 1, the tube 24 is a straight tube, of the <<I-Tube>> type.

Alternatively (not shown) the tube 24 is a tube which has a bent lower end, of the <<J-Tube>> type.

The tube 24 extends vertically on the structure 16. It delimits an internal lumen 28 for letting through the flexible line 10. It opens downwards into the stretch of water 14 and opens upwards, advantageously above the surface of the stretch of water 14.

When the flexible line 10 is positioned through the tube 24, an upper portion of the curvature limiter 26 is engaged at the lower end of the tube 24 and obturates the tube 24 downwards.

In the example illustrated in FIG. 2, the flexible line 10 is a flexible tubular pipe for transporting fluid interiorly delimiting a central passage 30 for circulation of fluid. That this pipe, also called <<rising pipe>> or <<riser>> is in particular intended for connecting a fluid reservoir on the bottom of the stretch of water to the connector 22 at the surface. This pipe is for example such as described in the normative API 17J and API RP17B documents published by the American Petroleum Institute (API).

Conventionally, as illustrated by FIG. 2, such a pipe advantageously includes an internal carcass 32 for load-spreading the radial crushing forces, an internal polymeric sealing sheath 34 and a pressure vault 36, for load-spreading the radial forces generated by the pressure of the transported fluid.

The flexible pipe also includes an internal ply 38 of tensile armors, an external ply 40 of tensile armors wound around the internal ply 38 in the opposite direction to the internal ply 38 and an outer polymeric sealing sheath 42.

In one alternative, the flexible pipe is without any internal carcass 30.

The carcass 30 is for example formed by means of a helically wound metal sheet.

The pressure vault 36 positioned around the sheath 34 is intended to spread the load of the forces related to the pressure prevailing inside the pipe. It is for example formed with a metal wire helically wound around the sheath which generally has a complete geometry in particular shaped as a Z, T, U, K, X, or I.

The tensile armor plies 38, 40 are for example formed with wound metal wires.

The internal sheath 34 is intended to confine the transported fluid in the lumen 30.

The external sheath 42 is intended to prevent fluid permeation from the outside of the flexible line 10 towards the inside and to protect the tensile armors.

In one alternative, the flexible pipe is without any pressure vault 36. It then advantageously includes an internal carcass 30, an internal sheath 34, at least two plies of crossed armors 38, 40, wound with an angle comprised between 50° and 60° relative to an axis of the pipe and an external sheath 42.

Such a flexible pipe, said to be with <<a balanced structure>>, is for example described in FR 2 743 858 or in the API RP 17B standard, March 2002 edition, in paragraphs §4.3.2.1 page 8, and §7.3.4.1.2 page 55.

According to the invention, the flexible line 10 includes at least one instrumented sheath 50 as illustrated in FIG. 3 or FIG. 4. In the example of FIG. 2, at least the one of the polymeric sheaths 34, 42, in particular the external sheath 42, consists of an instrumented sheet 50 according to the invention.

As illustrated by FIG. 3, the instrumented sheath 50 includes an electrically insulating polymeric tubular body 52 and a plurality of electrically conducting sensors 54A, 54B, 54C extending longitudinally along an axis A-A' of the sheath 50.

In the illustrated example, the body 52 is made on the basis of an electrically insulating polymer. This polymer is for example a polyolefin, such as polyethylene, a polyamide such as PA11 or PA12, or a fluorinated polymer such as polyvinylidene fluoride (PVDF).

The body 52 generally has a thickness of less than 30 mm and in particular comprised between 3 mm and 20 mm. It generally has a length of more than 5 m.

The electric conductivity of the polymeric tubular body 52, taken in its bulk, away from the sensors 54A to 54C, is less than $10^{-8}$ S/cm, typically of the order of $10^{-10}$ S/cm for polyolefins such as polyethylene and of the order of $10^{-12}$ S/cm for polyamides.

The sensors 54A to 54C are each formed by a longitudinal wire member or cord 56. In the illustrated example in FIG. 3, the cords 56 are positioned on the external surface of the tubular body 52.

The width of the cords 56 is less than 20/1000 times their length. This width for example is less than 20 mm.

Each sensor 54A to 54C has greater electric conductivity than that of the tubular body 52, in particular at least 10 times greater than that of the tubular body 52, and preferably at least 100 to 1,000 times greater than that of the tubular body.

This electric conductivity is for example greater than $10^{-6}$ S/cm.

Each sensor 54A to 54C extends longitudinally along the sheath 50 over a minimum length comprised between ten meters and twenty meters, preferentially fifteen meters. In an embodiment, each sensor 54A to 54C is advantageously parallel to the axis A-A' of the sheath 50.

The sheath 50 includes at least two sensors 54A, 54B, 54C spaced apart angularly relatively to each other. The sensors are for example connected to each other at least at one end. According to an alternative of the invention, the sensors 54A to 54C are spaced apart angularly from each other but are not necessarily connected together.

The sheath 50 thus has, on at least one portion of its length, at least two sensors 54A, 54B, axially located facing each other, in particular parallel with each other.

Each sensor 54A, 54B is separated from the adjacent sensor 54B, 54A with an insulating angular segment 58 of the tubular body 52 able to electrically insulate the sensors 54A, 54B from each other.

In the example illustrated in FIG. 3, the sheath 50 comprises a plurality of sensors 54A to 54C angularly distributed around the axis A-A' and separated from each other with insulating angular segments 58 of the tubular body 52.

Advantageously, the sensors 54A to 54C of each pair of adjacent sensors 54A to 54C are spaced apart by an angle of 30°, taken relatively to a central axis of the line 10, for a flexible line with an inner diameter equal to six inches. For flexible lines, the inner diameter of which is greater than six inches, said sensors 54A to 54C are spaced apart by an angle comprised between 10° and 20°, preferentially 15°.

In an embodiment, the sensors 54A, 54B are grouped in pairs. The sensors 54A, 54B of each pair are electrically connected to each other, in particular at their axial ends.

This electric connection, symbolized by reference 60, is for example formed by a conductive segment connecting the axial ends of two sensors 54A, 54B or by a sensor segment, of the same nature as the sensors 54A, 54B forming an electric connection between the sensors 54A, 54B.

In a first embodiment, each cord 56 is formed with a polymeric matrix containing electrically conducting fillers. The polymeric matrix is solid or without any continuous cavity over the whole of the length of the cord 56.

In particular, the polymeric matrix of each cord 56 is made on the basis of an electrically insulating polymer in the absence of fillers. This polymeric matrix is for example made in the same polymer as the one making up the tubular body 52.

In this case, the dispersed fillers ensure the overall electric conductivity of the cord 56. These fillers are for example carbon black particles, carbon nanotubes, graphene, metal particles.

The mass percentage of fillers in the polymeric matrix is generally comprised between 0.5% by mass and 5% by mass.

In the case when the polymeric matrix of the cord 56 is of the same nature as the polymer forming the body 52, for example when the body 52 is a thermoplastic PP+EPDM elastomer and the polymeric matrix of the cord 56 is in PP, no binder is required for attaching the cord 56 and the tubular body 52 together.

Alternatively, a binding agent such as polyethylene grafted with maleic anhydride is added for improving compatibility between the polymeric matrix of the cord 56 and the polymer forming the body 52. This is in particular the case if the body 52 is made from polyethylene (PE) and that the cord 56 is formed from polyamide (PA). However the binding agent depends on the nature of the polymers used for applying the tubular body 52 and the cord 56. In the case when the tubular body 52 is made from polyethylene (PE), the cord 56 being formed from polypropylene (PP), a binding agent will for example be selected from the family of C2/C4 terpolymers such as the reference BORSEAL™, marketed by Boréalis.

In a second embodiment, the cord 56 is made on the basis of an intrinsically conductive polymer material. This polymeric material is for example selected from polyacetylenes, polyanilines, polypyrroles or polythiophenes. In this case, the electric conductivity of the polymeric material is for example greater than $10^{-4}$ S/cm. a binding agent may be used for improving the compatibility between the polymeric matrix of the cord 56 and the polymer forming the body 52.

In the example illustrated in FIG. 3, each sensor 54A, 54B, 54C is positioned on the external face of the tubular body 52, advantageously in grooves made in the external face of the tubular body 52 for receiving the cords 56.

In this case, each cord 56 is advantageously flush with the outer face of the body 52 and is accessible in any point of the sheath 50 along the latter.

In the embodiment illustrated in FIG. 4, the cords 56 are embedded in the tubular body 52 and are only accessible from the outside at the ends of the sheath 50.

In an embodiment, the measuring apparatus 20 is intended to perform the electric measurements between two points of the sheath 50, in particular between two points 60A, 60B located on two sensors 54A, 54B of a pair of sensors 54A, 54B electrically connected to each other.

The measurement apparatus 20 is able to measure the conductivity or the resistivity between two measurement terminals 62A, 62B intended to be electrically connected to the points 60A, 60B respectively. The measurement apparatus 20 is advantageously a multimeter.

This electric conductivity is for example measured by means of a measurement apparatus such as a multimeter, for example an ohmmeter, by the following method which consists in applying wires, connected to the measurement apparatus, to the accessible ends or <<terminals>> of each of the conductors 54A and 54B in order to check whether there is electric continuity or abrasion of the tubular body 52. A conducting material facilitates the passing of the current, conversely to an insulating material which does not itself let the current through. Therefore if the measurement apparatus indicates a low resistance value, for example less than or equal to the rated resistance value of the sensor 54A, 54B, this means that the tubular body 52 is complete. Conversely, if the measurement apparatus indicates a high resistance value, for example strictly greater than the rated resistance value of the sensor 54A, 54B, this means that partial abrasion or total failure of at least one of said sensors 54A and 54B has occurred and therefore the body 52 has been subject to degradation.

In another embodiment, the measurement apparatus 20' is intended to make propagation measurements of an electric signal in each point 60A, 60B located on two sensors 54A, 54B either connected together or not connected.

The measurement apparatus 20' is able to measure electric continuity (and indirectly conductivity or resistivity) between two measurement terminals 62A, 62B intended to be respectively electrically connected to the points 60A, 60B. The measurement apparatus 20' is advantageously a time domain reflectometer.

In this case, electric continuity (and indirectly electric conductivity) of the sensors 54A to 54C is measured by a pulse reflection method called TDR for Time Domain Reflectometry. It is possible to detect and localize all discontinuities which may exist along a transmission line or an electrically conducting cable.

By means of a measurement apparatus such as a time domain reflectometer which has been connected to the ends or <<terminals>> of two conductors (here the sensors 54A, 54B) very close to each other, an electric pulse is sent into two of the sensors 54A, 54B. The wave then propagates over the whole of the length of said sensors 54A, 54B. If a positive reflected signal is re-emitted towards the reflectometer, this means that the emitted signal has encountered the tubular body 52 formed by an electrically insulating material at the end of said sensors 54A, 54B and that there is then no flaw in the presence of this area of said tubular body 52. This amounts to considering an open electric circuit. Conversely, if a negative reflected signal re-emitted towards the reflectometer, this means that at a certain point of one of said sensors 54A, 54B, there exists a flaw and therefore that the tubular body 52 has been subject to localized abrasion. This amounts to considering that there is a <<short-circuit>>. The time taken by the re-emitted signal for returning to the reflectometer gives information on the position where the fault is located along the sensors 54A, 54B and the amplitude of the re-emitted signal gives information on the nature of the encountered flaw.

In one alternative, the measurement is made by sending an electric pulse into one single sensor 54A to 54C.

Examples of techniques for measuring electric continuity are given in Part IN-118-1 of the <<Techniques de l'Ingénieur>> (dated from May 2010), entitled <<Diagnostic filaire>> (Wire diagnostics) or in the HN 41-M-1 specification from the Electricité de France Corporation, dated from July 1979.

The tubular body 52 is advantageously made by extrusion. In a first embodiment of the sheath of FIG. 3, the cord 56 is applied on the external face of the tubular body 52 by a derived co-extrusion method. For this purpose, in order to facilitate the setting into place of the cords 56, longitudinal grooves are advantageously made during the extrusion of the body 52. The cords 56 are formed by extrusion, and are deposited on the outer face of the body 52, for example in grooves.

In one alternative, the conducting cords 56 are made before the tubular body 52, in particular by extrusion. They are then integrated into the fluid polymer intended to form the body 52 so as to be attached onto the outer face of the tubular body 52.

Figure 5:
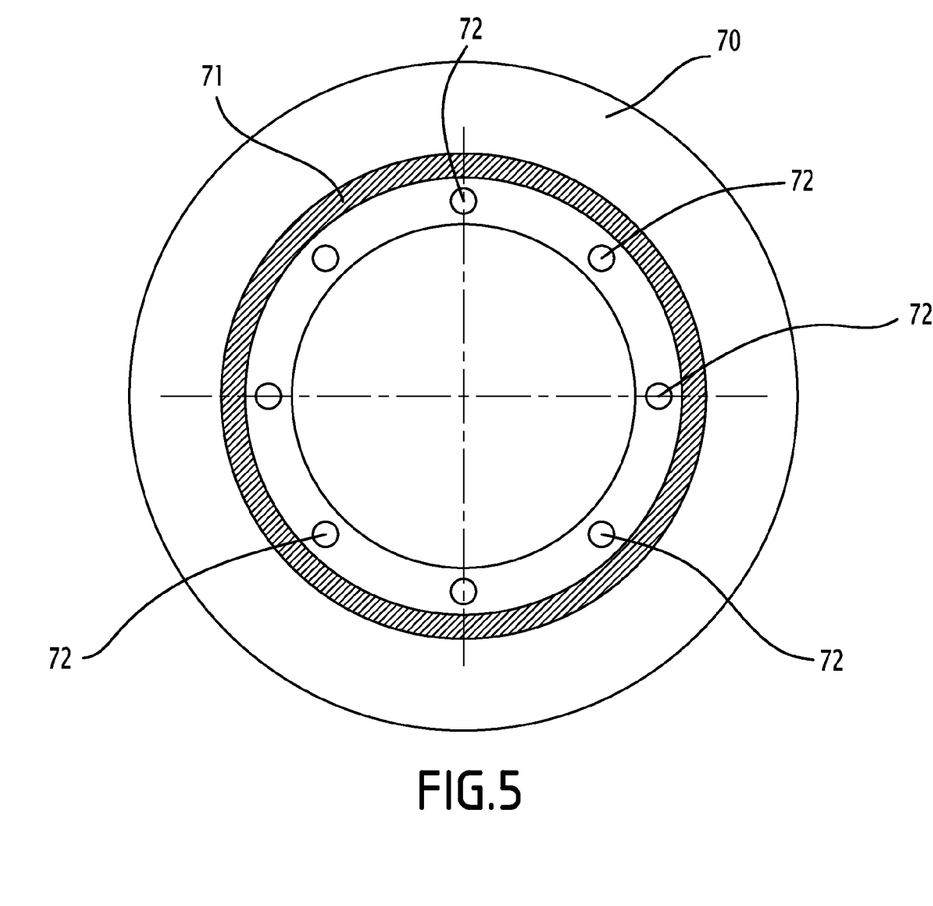
FIG. 5 is a view of one face of a die intended for making the sheath of FIG. 4.
Figure 6:
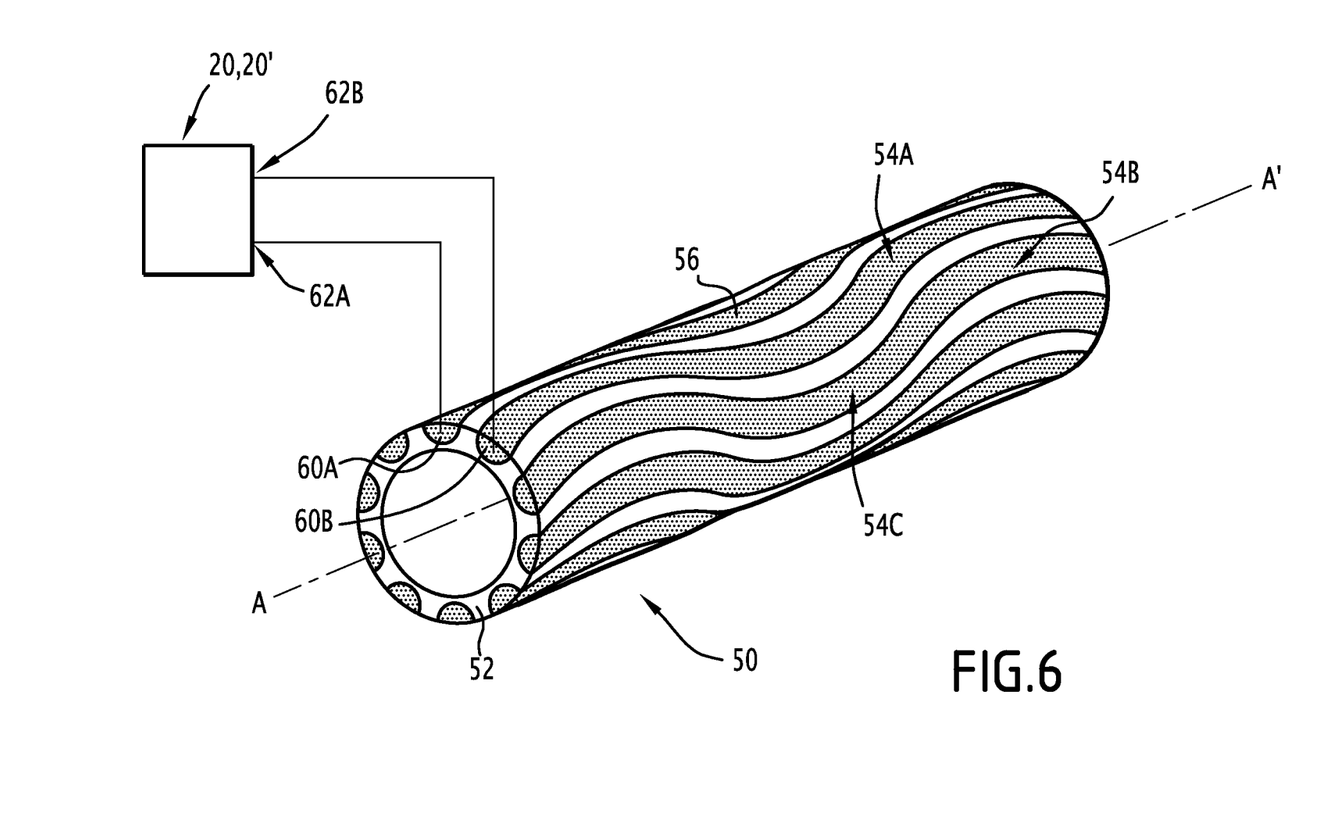
FIG. 6 is a view similar to FIG. 3 of another example of a flexible sheath according to the invention.

In order to make the sheath according to FIG. 4, the body 52 and the cords 56 are for example co-extruded simultaneously by means of a die schematically illustrated in FIG. 5. As illustrated in FIG. 5, this die includes a ring-shaped passage 71 intended to form the body 52 and a plurality of injection pipes 72 for the cords 56 positioned in the ring-shaped passage 70 for bringing the fluid material intended to form the cords 56.

The fluid polymer intended to form the sheath 52 is brought into the ring-shaped passage 71. The polymeric material intended to form the cords 56, optionally containing fillers, is brought through the pipes 72 so as to be integrated into the polymeric material extracted through the ring-shaped passage 71.

In one alternative, each cord 56 is made separately, before extrusion of the tubular body 52. Each cord 56 is then integrated into the tubular body 52 upon extrusion of the latter.

A method for measuring the integrity of the flexible line 10 positions through the facility 12 will now be described.

Initially, with reference to FIG. 1, the flexible line 10 was moved upwards through the guiding tube 24 from the lower end of the tube 24 to the upper end in order to be connected to the connector 22.

During this displacement, and in certain cases, the sheath 50 of the line 10, advantageously its external sheath 42, risks being subject to premature wear and/or an abrasion phenomenon, in particular by friction between the line 10 and the tube 24.

This phenomenon may occur upon mounting the flexible line 10 in the facility 12, or subsequently, upon fluid exploitation through the facility 12.

In this case, when the sheath 50 is degraded, wear or even local failure of at least one of the sensors 54A to 54C has occurred.

A first method for measuring integrity according to the invention includes a first step for electrically connecting the terminals 62A, 62B of the electric apparatus 20 to a first measurement point 60A on a first sensor 54A and to a second measurement point 60B on a second sensor 54B electrically connected to the first sensor 54A.

Next, a resistivity and/or conductivity measurement between the points 60A, 60B is made by the measurement apparatus 20.

In the case when the sensors 54A, 54B are intact, conductivity is maximum, and the resistivity is minimum. If a failure of one of the sensors 54A, 54B has occurred, conductivity is minimum and resistivity is maximum.

In a first measurement method, applied to the sheaths 50 of FIGS. 3 and 4, the measurement is made by connecting the terminals 62A, 62B of the apparatus 20 to the respective ends of two sensors 54A, 54B. This connection is for example carried out at the surface on measurement points 60A, 60B located at the upper ends of the sensors 54A, 54B.

In one alternative, applicable to the sheath 50 of FIG. 3, successive measurements are made by electrically connecting the terminals 62A, 62B of the measurement apparatus 20 to successive measurement points 60A, 60B located on the outer face of the sheath 50 at the cords 56 which appear on this face.

Successive measurements may be made in various longitudinal positions along the axis A-A' of the sheath 50, along its portion in the open air, at platform level, by qualified personnel or else along its immersed portion, by means of a remote controlled vehicle or a ROV (Remotely Operated Vehicle). It is thus possible to evaluate at which level a possible failure of one of the sensors 54A, 54B has occurred.

This method is designated by the term of <<pin method>>.

A second method for measuring integrity according to the invention includes a first step for electrically connecting at least one of the terminals 62A, 62B of the measurement apparatus 20' respectively to a measurement point 60A, 60B on a sensor 54A, 54B.

Next, an electric pulse is sent in order to carry out a measurement of electric continuity/discontinuity (resistivity and/or conductivity) between the points 60A, 60B with the measurement apparatus 20', as explained above.

In the case when the sensors 54A, 54B are intact, the re-emitted signal is identical with the emitted signal. And, if a failure of one of the sensors 54A, 54B has occurred, the reemitted signal is negative and is amplitude varies according to the seriousness of the observed failure.

In a second measurement method, applied to the sheaths 50 of FIGS. 3 and 5, the measurement is carried out by connecting the terminals 62A, 62B of the apparatus 20' to the respective ends of the sensors 54A, 54B or 54C. This connection is for example carried out at the surface of the measurement points 60A, 60B or 60C located at the upper ends of the sensors 54A, 54B or 54C.

The measurement of integrity is advantageously applied after setting into place the flexible line 10 on the structure 16, before operating the flexible line 10, or further subsequently upon utilizing the flexible line 10.

In an alternative illustrated in dotted lines in FIG. 3, both terminals 62A, 62B of the measurement apparatus 20 are connected to respective measurement points 60A, 60B spaced apart longitudinally on a same sensor 54A, 54B. In this case, the neighboring sensors 54A, 54B are not necessarily connected together through a connection 60.

In another alternative, the sheath 50 has a single sensor 54A advantageously having a length of less than 110% of the length of the sheath 50.

In other alternatives (not shown), the flexible line 10 is an umbilical as defined by the API 17E an (API RP 17I)

standard. This umbilical is intended to convey a hydraulic control fluid, electric power, or a signal for conveying information.

In another alternative, the flexible line 10 is a bundle of electric cables.

In the preceding examples, the wire sensors 54A to 54C are placed in one of the sheaths 34, 42. More generally, the sensors 54A to 54C may be placed in any polymeric sheath of the flexible line.

What is claimed is:

1. A method for monitoring the integrity of a flexible line extending through a fluid exploiting facility, the flexible line comprising at least one sheath including a polymeric tubular body, wherein the method comprises the following steps:
   providing at least one wire sensor in contact with the tubular body, said or each sensor including a polymer matrix having greater electric conductivity than that of the tubular body,
   measuring an electric quantity representative of the integrity of the tubular body, in at least one measurement point located on the sensor.

2. The method according to claim 1, wherein the flexible line is engaged through a protective tube present in the fluid exploiting facility, at least one portion of the sensor being positioned in the protective tube.

3. The method according to claim 1, wherein said or each sensor is embedded in the thickness of the tubular body or is attached onto one face of the tubular body.

4. The method according to claim 1, wherein said or each sensor is made on the basis of an intrinsically conductive polymeric matrix.

5. The method according to claim 1, wherein said or each sensor is made on the basis of an insulating polymer matrix filled with conductive particles.

6. The method according to claim 1, including putting a first measurement point located on the sensor into contact with a first terminal of an apparatus for measuring an electric quantity, and putting a second measurement point located on the sensor or on an additional sensor into contact with a second terminal of the measurement apparatus, the measurement apparatus is a multimeter, the electric quantity.

7. The method according to claim 1, including injecting an electric signal into the sensor and the measurement of an electric signal having propagated through the sensor in at least one measurement point for determining the electric continuity of the sensor.

8. The method according to claim 1, including providing at least one first wire sensor and of at least one second wire sensor in contact with the tubular body (52), each sensor including a polymeric matrix having greater electric conductivity than that of the tubular body, the first sensor and the second sensor being at least partly spaced apart angularly relatively to each other, relative to an axis of the tubular body.

9. The method according to claim 8, wherein at least one first downstream point of the first sensor, is electrically connected with a second downstream point of the second sensor said or each measurement point being respectively located away from the first downstream point and away from the second downstream point.

10. A flexible line intended to extend through a fluid exploiting facility, the flexible line comprising at least one sheath including a polymeric tubular body, the sheath including at least one wire sensor in contact with the tubular body, each sensor including a polymeric matrix and having greater electric conductivity than that of the tubular body, each wire sensor comprising a measurement point located at the upper end of the wire sensor, the measurement point being configured to be electrically connected to at least one measurement terminal of a measurement apparatus.

11. The line according to claim 10, wherein the tubular body contains or delimits a passage for circulation of fluid.

12. The line according to claim 10, wherein the sensor is made on the basis of an intrinsically conductive polymer, or of an insulating polymer filled with conductive particles.

13. The line according to claim 10, including at least one first wire sensor and at least one second wire sensor in contact with the tubular body, said or each sensor including a polymeric matrix and having greater electric conductivity than that of the tubular body, the first sensor and the second sensor being at least partly spaced apart angularly relatively to each other, relative to an axis of the tubular body.

14. A measurement kit, including a flexible line intended to extend through a fluid exploiting facility, the flexible line comprising at least one sheath including a polymeric tubular body, the sheath including at least one wire sensor in contact with the tubular body, each sensor including a polymeric matrix and having greater electric conductivity than that of the tubular body, the kit including an apparatus for measuring an electric quantity in at least one measurement point located on the sensor.

15. A method for manufacturing a flexible line according to claim 10, comprising:
   extruding the polymeric tubular body;
   positioning in contact with the tubular body at least one wire sensor, said or each sensor including a polymeric matrix and having greater electric conductivity than that of the tubular body, each wire sensor comprising a measurement point located at the upper end of the wire sensor, the measurement point being configured to be electrically connected to at least one measurement terminal of a measurement apparatus.

16. The method according to claim 15, wherein said or each sensor is co-extruded with the tubular body simultaneously so as to be positioned in the thickness or on one face of the tubular body.

17. The method according to claim 15, comprising making the said or each sensor before extruding the tubular body, and then positioning of each sensor in the thickness or on one face of the tubular body upon extruding the tubular body.

18. The method according to claim 2, wherein the protective tube is a vertical tube secured to a surface structure of the facility.

19. The method according to claim 4, wherein the polymer matric is based on a polymer selected from polyacetylenes, polyanilines, polypyrroles, and polythiophenes.

20. The method according to claim 5, wherein the electrically conducting particles is selected from carbon black particles, carbon nanotubes, grapheme, metal particles or mixtures thereof.

21. The method according to claim 6, wherein the measurement apparatus is a multimeter, the electric quantity being the conductivity or resistivity.

22. The line according to claim 13, wherein the first sensor and the second sensor extend facing each other, longitudinally relative to the tubular body.

23. A measurement kit, including a flexible line intended to extend through a fluid exploiting facility, the flexible line comprising at least one sheath including a polymeric tubular body, the sheath including at least one wire sensor in contact with the tubular body, each sensor including a polymeric matrix and having greater electric conductivity than that of the tubular body, the kit including an apparatus for measuring an electric quantity in at least one measurement point located on the sensor, wherein the measurement apparatus is advantageously a measurement apparatus intended to measure an electric quantity between measurement points spaced apart from each other or an apparatus for measuring an electric signal propagating through the sensor.

* * * * *